(12) United States Patent
Wilke

(10) Patent No.: US 6,464,669 B2
(45) Date of Patent: Oct. 15, 2002

(54) CATHETER PROTECTOR

(76) Inventor: Mark Wilke, 200 N. Ashbury Ave., Bolingbrook, IL (US) 60440

( * ) Notice: Subject to any disclaimer, the term of this patent is extended or adjusted under 35 U.S.C. 154(b) by 106 days.

(21) Appl. No.: 09/741,557

(22) Filed: Dec. 19, 2000

(65) Prior Publication Data

US 2001/0034505 A1 Oct. 25, 2001

Related U.S. Application Data

(63) Continuation-in-part of application No. 09/478,484, filed on Jan. 6, 2000, now abandoned, which is a continuation of application No. 08/897,462, filed on Jul. 21, 1997, now abandoned.

(51) Int. Cl.[7] .............................................. A61M 5/32
(52) U.S. Cl. ..................................................... 604/179
(58) Field of Search ........................ 604/174, 179–180, 604/523; 128/DIG. 6, 26, 878, 882, 898; 602/1, 3, 5–6, 20–21; 2/69, 59, 250, 16, 249

(56) References Cited

U.S. PATENT DOCUMENTS

| | | | |
|---|---|---|---|
| 3,160,158 A | 12/1964 | Rayhart | 128/349 |
| 3,835,854 A | 9/1974 | Jewett | 128/214.4 |
| 4,470,410 A | * 9/1984 | Elliott | |
| 4,591,356 A | 5/1986 | Christie | 604/179 |
| 4,596,552 A | * 6/1986 | DeVries | 604/118 |
| 4,610,245 A | 9/1986 | Biearman | 128/82 |
| 4,856,112 A | 8/1989 | Effle | 2/59 |
| 4,964,176 A | 10/1990 | Previdi | 2/242 |
| 5,048,122 A | 9/1991 | Prieur | 2/69 |
| 5,188,608 A | 2/1993 | Fritts | 604/179 |
| 5,190,530 A | 3/1993 | Greff et al. | 604/179 |
| 5,642,525 A | * 7/1997 | Ketola | 2/16 |
| 5,720,713 A | 2/1998 | Hutchison | 602/3 |
| 5,776,105 A | 7/1998 | Corn | 604/174 |
| 5,817,038 A | 10/1998 | Orange et al. | 602/3 |
| 5,832,928 A | 11/1998 | Padilla, Jr. | 128/877 |

* cited by examiner

Primary Examiner—Brian L. Casler
Assistant Examiner—LoAn H. Thanh
(74) Attorney, Agent, or Firm—Clifford Kraft

(57) ABSTRACT

A catheter protector designed to be of assistance to patients using a Peripherally insterted central catheter. The catheter is inserted into a vein in the patients arm, usually at the elbow. The catheter has an attached tube which is usually pinched off. The protector can be an elastic tubular sleeve with a zipper or other attachment means at its lower end running longitudinally to a point one-half to three-quarters of the way up the bottom half of the tube. The zipper or attachment is opened, and the sleeve is slipped over the catheter. The attached tube can then be coiled up inside the sleeve and the zipper closed. The device protects the site and tube against pulling and contamination. The zipper or attachement can be opened any time to administer drugs or replace the catheter. The device can optionally contain an inner plastic layer with an optionally inner layer of gauze to further protect the insertion site. The invention can be worn 24 hours a day including wear during bathing.

5 Claims, 6 Drawing Sheets

CATHETER PROTECTOR

This is a continuation-in-part of application Ser. No. 09/478,484 filing date Jan. 6, 2000, now abandoned which was continuation of application Ser. No. 08/897,462 filing date Jul. 21, 1997 now abandoned.

BACKGROUND

1. Field of the Invention

This invention relate s generally to the field of protective devices and more particularly to a protective sheath or sleeve for use with peripherally inserted central catheters.

2. Description of Related Art

Peripherally inserted central catheters (PICC) are devices commonly used by physicians to administer drugs to patients on a continuing basis. The PICC may be implanted into the patients vein for an extended interval. Drugs are either self-administered or are administered by medical personnel when the patient returns periodically to a medical facility or when medical personnel administer drugs at a patient's home. The PICC is a soft, flexible tube that can be inserted into a patients vein surgically.

Usually the site of implant is taped or otherwise protected from infection, and the PICC is equipped with an extendable plastic tube that can be used for drug administration. With prior art methods, there is a constant danger of pulling or otherwise interfering with this apparatus during normal daily activities or during sleep. This can lead to pain and danger of infection. In addition, normal activities can cause dirt or bacteria to enter the plastic tube if some special precaution is not taken to keep it sterile.

It is usual for medical personnel to supply a small mesh net with a PICC implant that ties to the arm at the top and bottom and holds the PICC line very loosely. This arrangement is very clumsy.

Prior art methods have included restrictive garments mainly designed for children that actually prevent the patient from gaining any access to the PICC. Such a garment is bulky, hot, and difficult to put on. In addition, since it does not allow any access to the PICC, it must be removed, or at least opened completely, to administer drugs. This type of protection for the PICC is not desirable for an adult patient, especially a patient who must self-adminster drugs.

What is badly needed is a protective method and apparatus for PICC devices that allows the patient freedom of movement, allows easy administration of drugs through the PICC, keeps the PICC clean, and prevents pulling on the PICC through normal daily activities. A sleeve device is ideal for this application since it can be made long or short for different seasons. It allows total freedom of movement, and it allows easy access for drug administration. A similar device could be used for a leg if for some reason a PICC was implanted on a leg.

SUMMARY OF THE INVENTION

The present invention relates to an apparatus designed to be of assistance to patients using PICC's. The invention embodies a sleeve made of material or plastic, preferably elastic, that can slide over a patient's arm or leg to hold a PICC medical device firmly in place. Various embodiments of the invention have sleeves that open different ways to reach the PICC. Also various means of closure such as zippers and synthetic materials that adhere when pressed together can be used. An example of such material is a loop/hook combination sold under the trade name of "Velcro" (it should be noted that when the term "Velcro" is used in this application, it refers to any product with pieces that adhere when pressed together).

The invention relates to a sleeve-like tube that may be slightly tapered with the larger diameter at the bottom. The tube may be used on an arm or leg. The tube can have elastic braids attached by sewing or other attachment means, or a zipper. The braids or zipper is used to make sure that the device fits snugly to the arm or leg where the PICC is located.

The sleeve-like tube of the invention can be constructed of various lengths and widths to fit different size arms or legs, and can optionally be made of an elastic stretch type cloth. The invention can be slid up the arm or leg, or wrapped around the arm or leg and tied or zipped up. Several embodiments of the invention are equipped with openings that open downward from the upper end to allow for access to a medical line into the PICC. Such openings could optionally open from the bottom.

The present invention also relates to a sleeve-like tube that fits around a patient's elbow to protect a site at the vein in the inside of the elbow. This embodiment of the present invention forms an elastic tube that begins above the elbow and ends near the wrist. The PICC can be rolled up inside this device. A zipper or other latching device can be provided to make access to the PICC easier.

The invention can also be used to protect other arm or leg treatments such as sutures, scrapes, etc. The invention can be dyed various colors to make it more attractive to purchase or to match attire for various situations or uses such as dress-up, garden work, etc.

BRIEF DESCRIPTION OF THE DRAWINGS

For a more complete understanding of this invention, reference should now be made to the embodiments illustrated in greater detail in the accompanying drawings and described below by way of examples of the invention, and in which.

It should be understood, of course, that the invention is not necessarily limited to the particular embodiments illustrated herein.

DETAILED DESCRIPTION OF THE INVENTION

Figure 1:
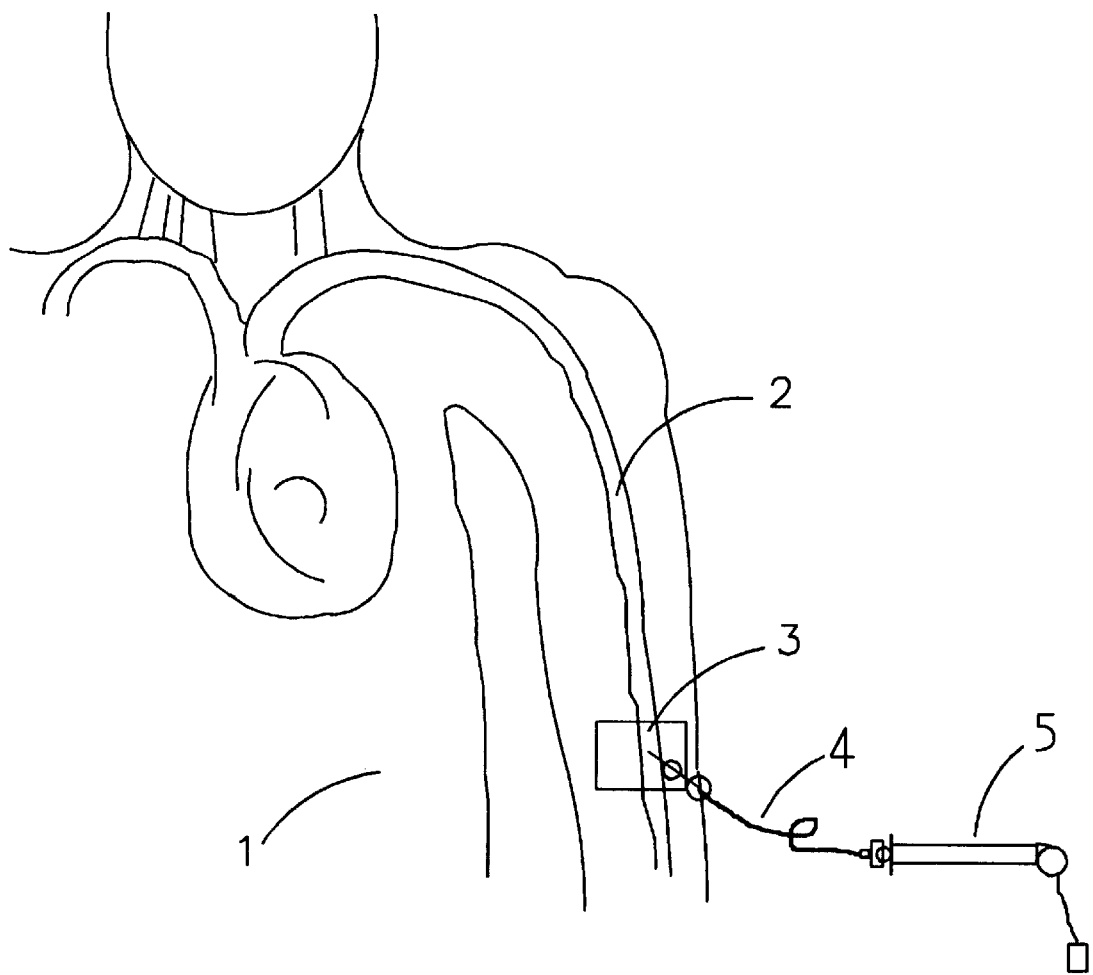
FIG. 1 shows a PICC inserted into a patients vein with the tube in an extended position.
Figure 2:
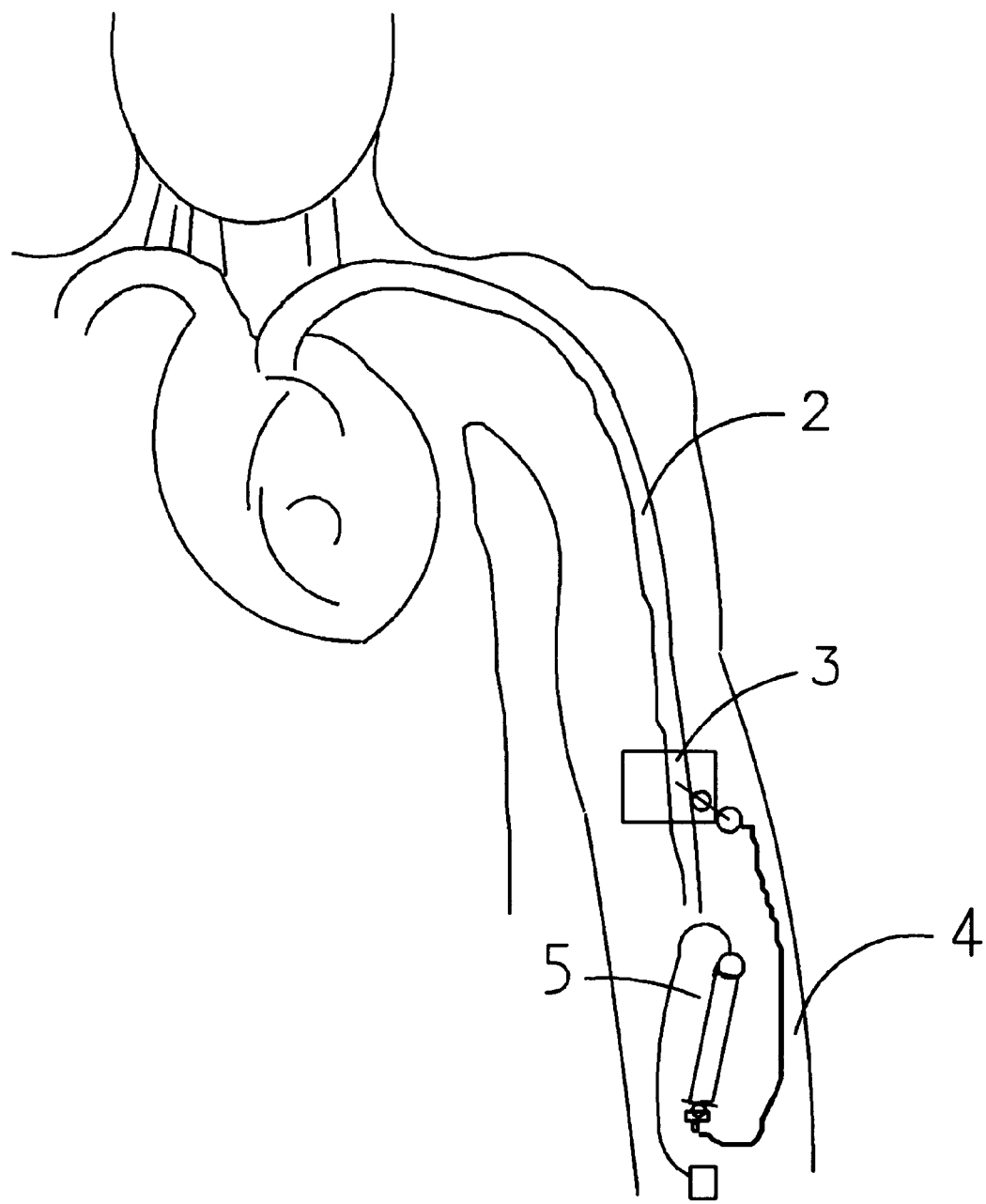
FIG. 2 shows a PICC inserted into a patients vein with the tube looped up.

FIGS. 1 and 2 show the use of a PICC. The patient 1 has an implant device 3 in his arm 2 at the site of a vein. The PICC uses a plastic tube 4 and a means of administering medication 5. FIG. 1 depicts the entire assembly in the extended state ready for the administration of medication. FIG. 2 shows the same PICC except that the plastic tube 4 is coiled up along the patient's arm 2. The medication means 5 is also placed close to the patient's arm 2. This is the normal, or non-administration state. This is the state the assembly is found in most of the time. It is this state where the danger of snagging, pulling, or contaminating the assembly or the implant site or device is high.

Figure 3:
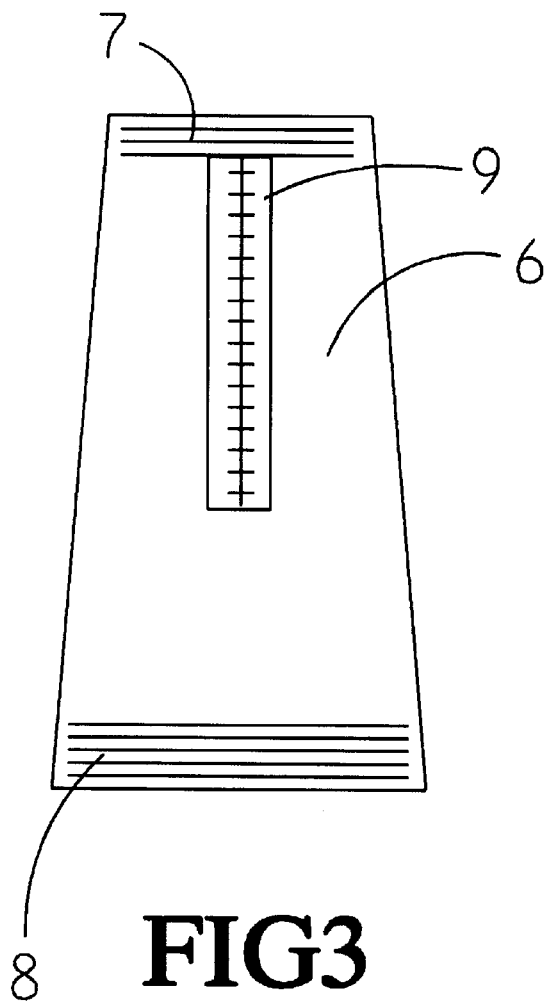
FIG. 3 shows a long sleeve embodiment of the invention with a zipper.

FIG. 3 shows a long sleeve embodiment of the invention. A sleeve 6 of material which can be elastic, cloth, or any other durable material, is cut from form a sleeve that fits over a human arm or leg. Since the dimensions of people's arms or legs vary, the invention can be made in many different sizes including different lengths and widths. At each end of the sleeve, a braid strip 7, 8 which can be rubberized elastic can be attached to the sleeve. This braid strip causes the sleeve to fit snugly and prevents it from moving up or down or from turning. The bottom braid strip (8) can be a different diameter than the top braid strip 7. A preferred diameter for the bottom braid strip (8) for a human arm is around 1 inch; however, this can vary considerably with different size sleeves. A preferred diameter for the top braid strip 7 for a human arm is around ¾ inches; however this can vary considerably with different size sleeves. While many lengths are possible, a preferred length for a human arm is around 14 inches.

The embodiment of FIG. 3 also contains a zipper 9 attached into the material of the sleeve 6. The zipper allows easy access to the PICC tubing for the administration of medication. While the zipper can be any length, the preferred length of the zipper on a long sleeve for a human arm is around 7 inches.

Figure 4:
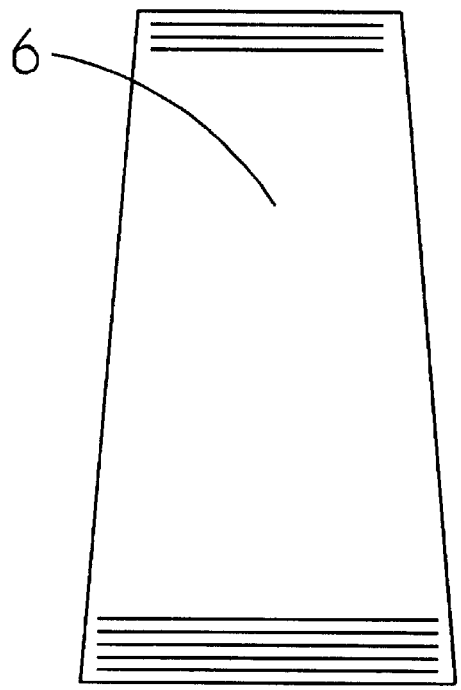
FIG. 4 shows a long sleeve embodiment of the invention without an opening.

FIG. 4 shows an embodiment of the invention which is a long sleeve with no zipper or other means of opening. This embodiment is simply formed into an elastic sleeve 6 that holds the PICC in place or covers and protects a wound, splint, or other medical site on an arm or leg. To get to a PICC with this embodiment, the patient must either remove the sleeve or pull it down (or up) out of the way.

Figure 5:
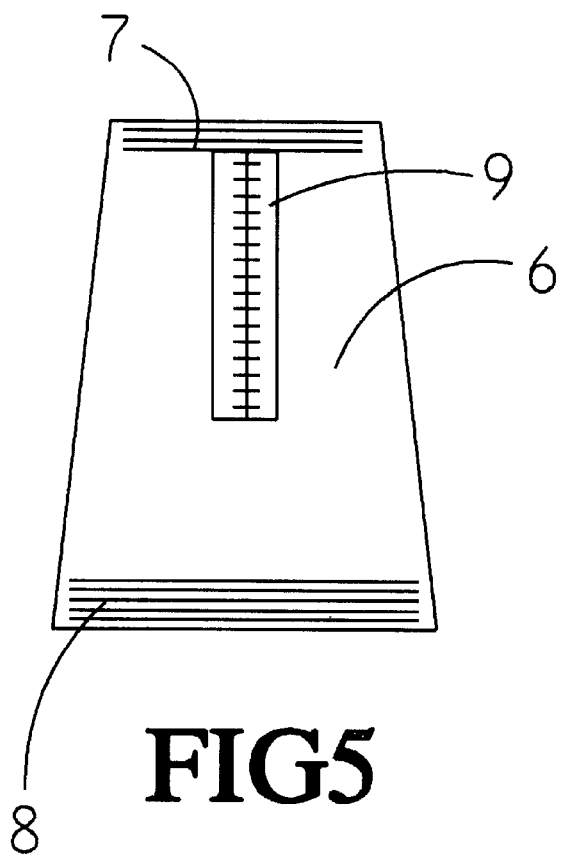
FIG. 5 shows a short sleeve embodiment of the invention with a zipper.

FIG. 5 shows an embodiment of the invention with short sleeves. It is very similar to the long-sleeve embodiment. This embodiment is move convenient for short sleeve shirts and summer wear. The preferred length of the short sleeve version is around 9 inches for a human arm; however, this may vary considerably with different sizes of the device. The embodiment in FIG. 5 also contains a zipper 9. Again, while this zipper can be any length, the preferred length of the zipper for the human arm is around 7 inches as with the long sleeve embodiment.

Figure 6:
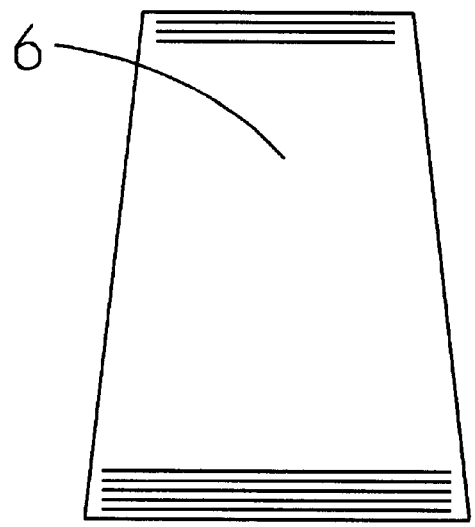
FIG. 6 shows a shot sleeve embodiment of the invention without an opening.

FIG. 6 shows a short sleeve embodiment similar to that shown in FIG. 5 except there is no opening. As with the embodiment of FIG. 4, the material is simply formed as a sleeve 6. Again, to get at a PICC or the site, the patient must either remove the sleeve or pull it down (or up) out of the way.

Figure 7:
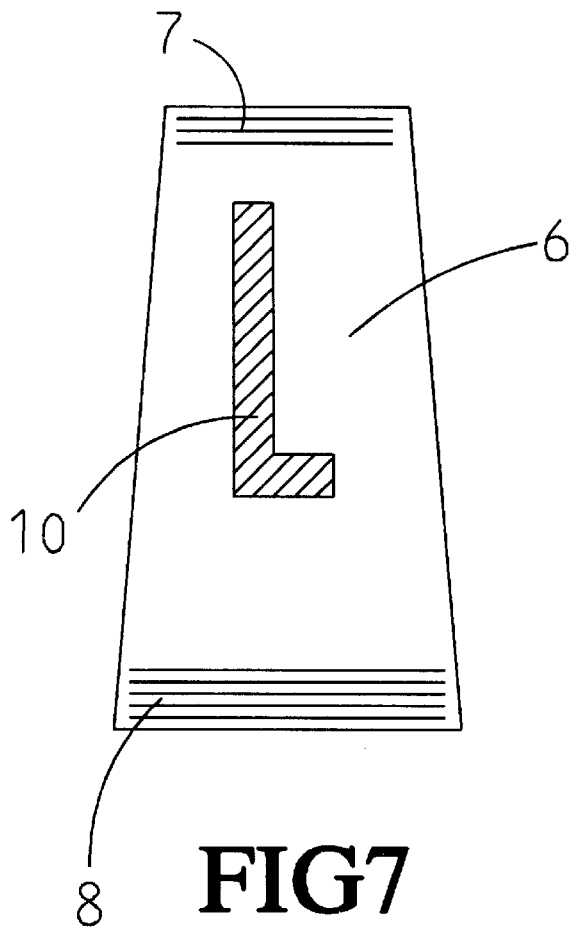
FIG. 7 shows a long sleeve embodiment of the invention with a Velcro opening.

FIG. 7 shows an embodiment of the long sleeve version of the invention that uses a Velcro seal 10 attached to the sleeve material 6. A Velcro seal (or any press-together seal) has the advantage over a zipper in that it is easier to open. This may be desirable for a patient who has trouble opening a zipper. While the Velcro seal can be any convenient length, the preferred length for the human arm is around 7½ inches long.

Figure 8:
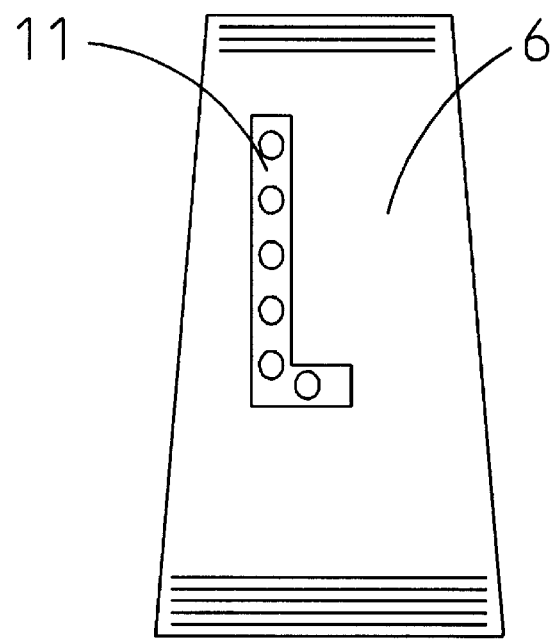
FIG. 8 shows a long sleeve embodiment of the invention with a snap seal.

FIG. 8 shows an embodiment of a long sleeve version of the invention that uses a set of snaps 11 attached to the sleeve material 6. Snaps can be made of any material, but may times are polymer material sold under the tradename "Nylon" (it should be noted that when the term "Nylon" is used in this application, it refers to any polymer material having properties similar to the material sold by DuPont Corporation under the trademark "Nylon"). The set of snaps can be any length, but the preferred length for a human arm is around 7½ inches. Snaps can also be made of metal, plastic, or other strong material. Snaps, zippers, velcro seals, and any press-together seal, as well as any other type of seal, can be generically described as closing devices.

The embodiments of FIGS. 7 and 8 can also be made as short sleeve embodiments previously described. As before, the preferred length of the short sleeve for the human arm is around 9 inches while the preferred length of the long sleeve embodiment is around 14 inches; this can vary considerably with different sizes of the invention. It should be noted that there is no preferred width since many different widths can be made to fit different arms or legs. The invention is generally made in different sizes to fit different individuals exactly like a garment.

Figure 9:
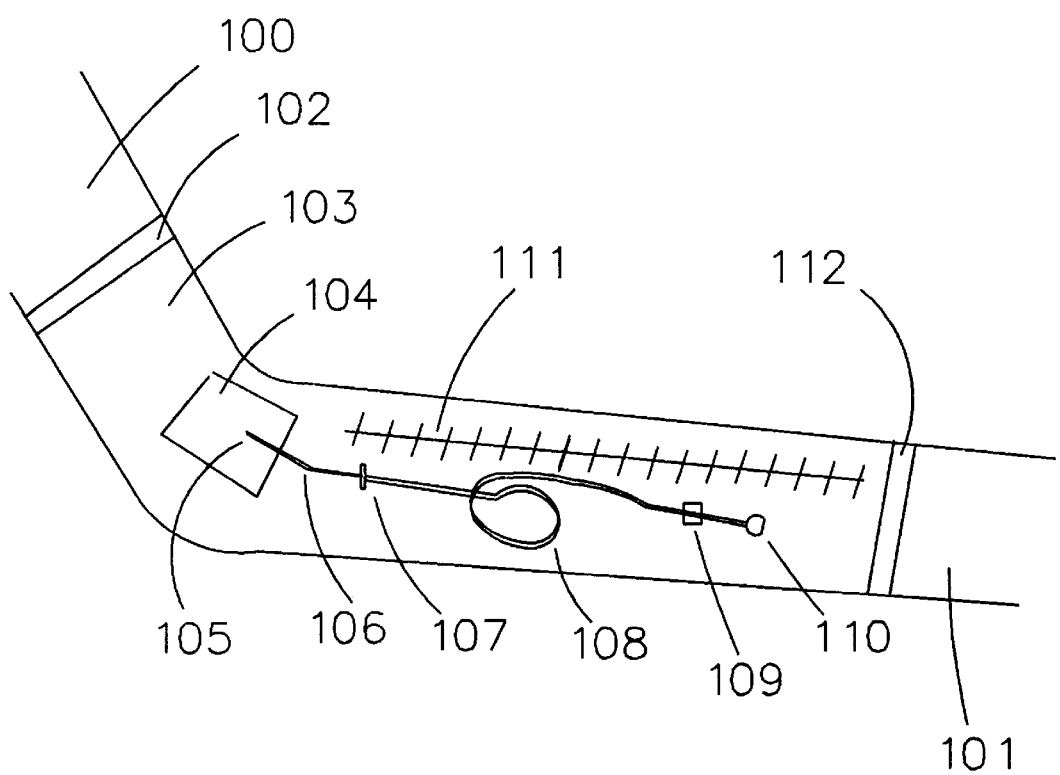
FIG. 9 shows an embodiment of the invention that extends from above the elbow to near the wrist.

FIG. 9 shows an important embodiment of the present invention comprising a sleeve 103 that extends both above and below the elbow. The arm is exposed above the sleeve 100 and below the sleeve 101 at the wrist. The sleeve 103 can contain a zipper 111 or other access device on its lower part. This zipper can extend all the way to the lower end of the sleeve to also assist in putting the sleeve on. This is to allow access to the PICC for the administration of drugs. The various parts of the PICC can be clearly seen in FIG. 9. A patch 104 covers the actual insertion site into the vein and is usually standard plastic medical tape applied by a nurse or physician at the time of the insertion. A connector section 106 attaches to the smaller catheter tube which is in the vein. This connector section 106 is usually of a diameter to mate to the smaller tube. A tubing junction 107, which is usually taped down, transitions to a slightly larger diameter tubing forming the catheter. The thicker catheter line 108 can be conveniently coiled under the sleeve where it is available to stretch out for drug administration. A pinch clip 109 is on the catheter and keeps a port 110 closed. The port 110 is used for drug administration by slipping a syringe into the port. The upper and lower end of the elastic sleeve can be secured by optional bands or braid strips 102, 112 to prevent slipping. The upper braid strip can be rubberized for greater gripping to prevent the sleeve from sliding downward.

The embodiment of FIG. 9 can be used by first inserting a catheter into a patient's arm, opening the zipper of the device, and running the catheter tube out of the zipper hole. The invention is then slid up and around the arm so that it extends above the elbow and securely covers the insertion site. Then the tube can be coiled up and placed in the sleeve, and the zipper can be closed. When it is desired to administer medication, the zipper can be opened and the tube uncoiled. A syringe is slipped into the port 110, and the pinch-clip 109 can be loosened to allow passage of the medication. When administration is done, the clip can be re-secured, the tube re-coiled, and the zipper closed.

The advantage of the embodiment shown in FIG. 9 over the previous embodiments is its much greater positional stability. While the other embodiments sometimes have a tendency to slip away from the insertion site, the embodiment of FIG. 9 does not do this, but rather remains in place since the upper braid strip, which can be rubberized for more grip, prevents it from moving further down. Since the sleeve is elastic, arm movement is in no way curtailed. The optional zipper allows easy application and removal as well as easy administration of medications. The material while getting wet during bathing, still provides protection for the catheter and keeps it clean. The sleeve can be worn while it dries.

While the embodiment of the present invention shown in FIG. 9 can be made different sizes, the optimum size, for an adult, is a sleeve around 14 inches long with a zipper around 7 inches long; any other size, especially smaller sizes for children, is within the scope of the present invention. This embodiment of the invention can be used continuously without removal for long periods of time. It provides excellent protection of the catheter and insertion site while bathing.

The various embodiments of the present invention are not restricted to use with human beings, but can also be used on animals. The invention is particularly useful for animals since they have more of a tendency than humans to twist or pull the PICC or to get dirt in the area of the site.

I claim:

1. A method of protecting a catheter comprising the steps of:
    inserting a catheter in a patient's vein near an elbow, said catheter having an attached tube;
    covering said insertion site with a protector;
    pinching off said catheter with a pinch clip;
    slipping a catheter protector over said patient's arm, said catheter protector being a tubular sleeve with a top part and a bottom part, said top part containing a braid strip and said bottom part containing a braid strip, said bottom part also containing a longitudinal zipper, said zipper being open when said catheter protector is slipped over said arm, said catheter tube being threaded out of said protector during said slipping operation;
    positioning said catheter protector so that the top part is above said elbow and the bottom part is below said elbow;
    coiling said attached tube inside said catheter protector;
    closing said zipper on said catheter protector;
    opening said zipper and uncoiling said catheter whenever necessary for administration of medication.

2. The method of claim 1 further comprising said catheter protector containing a plastic layer near its center to cover said vein.

3. The method of claim 2 further comprising said catheter protector containing a gauze layer under said plastic layer.

4. The method of claim 1 wherein said zipper is stainless steel.

5. The method of claim 1 further comprising the steps of:
    opening said zipper to replace said catheter;
    uncoiling said attached tube;
    removing said catheter from said vein;
    inserting a new catheter with a new attached tube in said vein;
    coiling said new attached tube inside said catheter protector;
    closing said zipper on said catheter protector.

* * * * *